United States Patent [19]
Inman et al.

[11] Patent Number: 5,949,537
[45] Date of Patent: Sep. 7, 1999

[54] IN-LINE CELL FOR ABSORPTION SPECTROSCOPY

[75] Inventors: Ronald S. Inman, Lyons; James J.F. McAndrew, Lockport, both of Ill.

[73] Assignee: American Air Liquide Inc., Walnut Creek, Calif.

[21] Appl. No.: 08/890,928

[22] Filed: Jul. 10, 1997

Related U.S. Application Data

[63] Continuation-in-part of application No. 08/711,504, Sep. 10, 1996, Pat. No. 5,818,578, which is a continuation-in-part of application No. 08/634,436, Apr. 18, 1996, abandoned.

[51] Int. Cl.⁶ .................................................. G01N 1/10
[52] U.S. Cl. ............................................................. 356/246
[58] Field of Search ................................... 356/432–444, 356/244, 246, 236; 250/343, 573, 576, 353; 359/850, 858, 861

[56] References Cited

U.S. PATENT DOCUMENTS

| | | | |
|---|---|---|---|
| 3,524,066 | 8/1970 | Blakkan | 250/218 |
| 3,994,603 | 11/1976 | Paschedag | 356/205 |
| 4,749,276 | 6/1988 | Bragg et al. | 356/246 |
| 4,934,816 | 6/1990 | Silver et al. | 356/409 |
| 4,937,461 | 6/1990 | Traina | 250/575 |
| 5,024,526 | 6/1991 | Van Redwitz | 356/73 |
| 5,065,025 | 11/1991 | Doyle | 250/343 |
| 5,173,749 | 12/1992 | Tell et al. | 356/437 |
| 5,220,402 | 6/1993 | Harvey | 356/246 |
| 5,352,902 | 10/1994 | Aoki | 250/575 |
| 5,360,980 | 11/1994 | Borden et al. | 250/573 |
| 5,459,569 | 10/1995 | Knollenberg et al. | 356/338 |
| 5,463,460 | 10/1995 | Fishkin et al. | 356/339 |
| 5,565,985 | 10/1996 | Fishkin et al. | 356/339 |
| 5,578,829 | 11/1996 | Talasek et al. | 250/343 |
| 5,818,578 | 10/1998 | Inman et al. | 356/246 |

FOREIGN PATENT DOCUMENTS

| | | |
|---|---|---|
| 0015170 | 9/1980 | European Pat. Off. . |
| 0 456 202 | 11/1991 | European Pat. Off. . |
| 0647845 | 4/1995 | European Pat. Off. . |
| 0 706 042 | 4/1996 | European Pat. Off. . |
| 0 768 525 | 10/1996 | European Pat. Off. . |
| 0 768 521 | 4/1997 | European Pat. Off. . |
| 3633931 | 4/1988 | Germany . |
| 4214840 | 11/1993 | Germany . |
| 2075213 | 11/1981 | United Kingdom . |
| 2165640 | 4/1986 | United Kingdom . |
| WO90/00732 | 1/1990 | WIPO . |

OTHER PUBLICATIONS

White, "Long Optical Paths of Large Aperture," J. Opt. Soc. Am., vol. 32 (1942), pp. 285–288.

T.A. Hu et al, "Improved Multipass Optics for Diode Laser Spectroscopy," Review of Scientific Instruments, vol. 64, No. 12, Dec. 1993, pp. 3380–3383.

Patent Abstracts of Japan, vol. 6, No. 59, JP 57–1953, Jan. 1982.

Fried et al, "Versatile Integrated Tunable Diode Laser System for High Precision: Application for Ambient Measurements of OCS," Applied Optics, vol. 30, No. 15, May 20, 1991, pp. 1916–1932.

(List continued on next page.)

*Primary Examiner*—Frank G. Font
*Assistant Examiner*—Michael P. Stafira
*Attorney, Agent, or Firm*—Burns, Doane, Swecker & Mathis, L.L.P.

[57] ABSTRACT

Provided is a novel in-line cell useful in absorption spectroscopy. The cell includes a sample region, a light entry port and a light exit port being the same or separate ports. Each port is in communication with the sample region and contains a light transmissive window. A mirror having a light reflective surface faces the sample region, and a heater effective to heat the light reflective surface is provided. The cell can be used to determine the concentration of molecular gas impurities in a sample. Particular applicability is found in semiconductor processing.

20 Claims, 3 Drawing Sheets

OTHER PUBLICATIONS

May, "Correlation–Based Technique for Automated Tunable Diode Laser Scan Stabilization," Rev. Sci. Instrum., vol. 63, No. 5, May 1992, pp. 2922–2926.

Eng et al., "Tunable Diode Laser Spectroscopy: An Invited Review," Optical Engineering, Nov./Dec. 1980, vol. 19, No. 6, pp. 945–960.

Lundqvist et al, "Measurements of Pressure–Broadening Coefficients of NO and $O_3$ Using a Computerized Tunable Diode Laser Spectrometer," Applied Optics, vol. 21, No. 17, Sep. 1, 1982, pp. 3109–3113.

Ahlberg et al, "IR–Laser Spectroscopy for Measurement Applications in the Industrial Environment," TR 85170, Dec. 85.

Höjer et al, "Measurements of Electric Field Strength in Gas Insulated High–Voltage Components Using Infrared Diode Laser Absorption Spectroscopy," Applied Optics, vol. 25, No. 17, Sep. 1, 1986; pp. 2984–2987.

Cassidy, "Trace Gas Detection Using 1.3 $\mu$m InGaAsP Diode Laser Transmitter Modules," Applied Optics, vol. 27, No. 3, Feb. 1, 1988; pp. 610–614.

Mitsui et al, "Development of New APIMS for the Detection of Trace Impurities in Special Gases," Proceedings of the 40th Annual Technical Meeting of the IES, Chicago, pp. 246–253 (1994).

Herriott et al, "Folded Optical Delay Lines," Applied Optics, vol. 4, No. 8, pp. 883–889 (Aug. 1965).

View A-A

IN-LINE CELL FOR ABSORPTION SPECTROSCOPY

CROSS REFERENCE TO RELATED APPLICATIONS

This application is a Continuation-in-Part of application Ser. No. 08/711,504 filed Sep. 10, 1996 and now U.S. Pat. No. 5,818,578, which application is a Continuation-In-Part of application Ser. No. 08/634,436 filed Apr. 18, 1996, abandoned. The contents of those applications are herein incorporated by reference.

BACKGROUND OF THE INVENTION

1. Field of the Invention

The present invention relates to a novel in-line cell useful in absorption spectroscopy. The present invention also relates to a system for performing an absorption spectroscopy measurement in a sample and to a semiconductor processing apparatus which comprise the novel in-line cell.

2. Description of the Related Art

Semiconductor integrated circuits (ICs) are manufactured by a series of processes, many of which involve the use of gaseous materials. Included among such processes are etching, diffusion, chemical vapor deposition (CVD), ion implantation, sputtering and rapid thermal processing.

Many of the gases used in these processes are highly reactive and tend to form deposits on surfaces with which they come into contact. When an in-line spectroscopic sensor is used to monitor a process in such aggressive atmospheres, deposits from the process gases tend to form on various surfaces of the sensor. As a result, sensor performance tends to deteriorate.

The sensitivity of detection of gas phase molecular species by absorption spectroscopy increases as the length of the light path through the sample increases, for constant pressure and concentration. The intensity of light reaching the detector is given by Beer's Law as follows:

$$I = I_o \cdot e^{-\alpha l c P}$$

where $I_o$ is the intensity of the incident radiation, $\alpha$ is the absorptivity, $l$ is the pathlength through the sample, $c$ is the concentration of the impurity in the sample (by volume), and $P$ is the total pressure of the sample. For small absorptions, the amount of light absorbed is given by $$I - I_o = \alpha l c P$$

In order to make $l$ large, it is frequently impractical to place the light source and detector very far apart and so "folded" light paths are often used, in which mirrors reflect the light back and forth through the sample gas many times.

The Herriott design is often preferred for tunable diode laser absorption spectroscopy (TDLAS). As shown in FIG. 1, the Herriott cell 100 uses two curved mirrors 102 mounted at opposite ends of a usually cylindrical gas sample cell 104. Simple multi-pass arrangements are often used, such as described in U.S. Pat. No. 3,524,066, to Blakkan, and U.S. Pat. No. 5,173,749, to Tell et al, the contents of which are herein incorporated by reference. A planar polygonal multipass cell is described by the present inventors in copending application Ser. No. 08/711,504, filed Sep. 10, 1996, the contents of which are herein incorporated by reference.

In the multipass cells described above, deposits formed on the reflective surfaces of the mirrors can reduce their reflectivity and hence the light intensity which reaches the detector after multiple reflections of the light beam. This reduction in light intensity reduces the measurement sensitivity and may eventually lead to a condition in which the sensor does not function at all.

Deposits on the mirrors can be removed by disassembling the sensor and mechanically cleaning the mirror(s). Such maintenance, however, is inconvenient and expensive. Avoidance thereof is, therefore, desirable.

To meet the requirements of the semiconductor processing industry and to overcome the disadvantages of the related art, it is an object of the present invention to provide a novel in-line cell useful in absorption spectroscopy. The in-line cell allows for accurate, in-situ absorption spectroscopy measurements which can be used, for example, to accurately and sensitively measure the concentration of gas phase molecular impurities in a sample. The problems associated with the formation of deposits on reflective surfaces of mirrors within the measurement cell are avoided or conspicuously ameliorated by the inventive cell.

It is a further object of the present invention to provide an absorption spectroscopy system which includes the inventive in-line cell.

It is further an object of the present invention to provide a semiconductor processing apparatus which includes the absorption spectroscopy system for performing in-situ measurements.

Other objects and aspects of the present invention will become apparent to one of ordinary skill in the art on a review of the specification, drawings and claims appended hereto.

SUMMARY OF THE INVENTION

According to a first aspect of the present invention, a novel in-line cell useful in absorption spectroscopy is provided. The in-line cell includes a sample region, a light entry port and a light exit port. The light entry port and light exit port can be the same or separate ports. Each port is in communication with the sample region and contains a light transmissive window. A mirror having a light reflective surface faces the sample region, and a heater effective to heat the light reflective surface is provided.

The in-line cell allows for accurate, in-situ absorption spectroscopy measurements which are useful, for example, to accurately and sensitively measure the concentration of gas phase molecular impurities, such as, e.g., methane, moisture (water vapor) and carbon dioxide, in a sample. In particular, the light reflective surfaces of the cell can be maintained in a deposit-free state.

According to a further aspect of the invention, a system for performing an absorption spectroscopy measurement is provided. The system includes an in-line cell as described above with reference to the first aspect of the invention. The inventive system further comprises a light source for generating a light beam which passes through the light entry port into the cell, and a main detector for measuring the light beam exiting the cell through the light exit port.

According to a third aspect of the invention, a semiconductor processing apparatus is provided. The apparatus comprises a vacuum chamber in communication with a vacuum pump for evacuating the vacuum chamber, and the inventive absorption spectroscopy measurement system described above.

BRIEF DESCRIPTION OF THE DRAWINGS

The objects and advantages of the invention will become apparent from the following detailed description of the preferred embodiments thereof in connection with the accompanying drawings, in which.

DETAILED DESCRIPTION OF THE PREFERRED EMBODIMENTS OF THE INVENTION

Figure 2A:
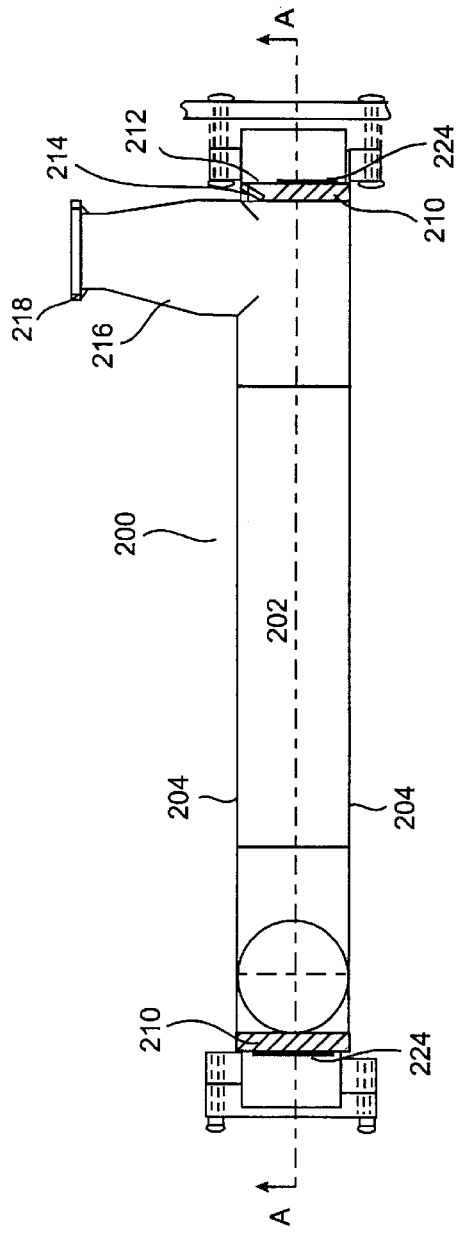
FIGS. 2A and 2B are top and side-sectional views of an in-line cell according to one aspect of the present invention.
Figure 2B:
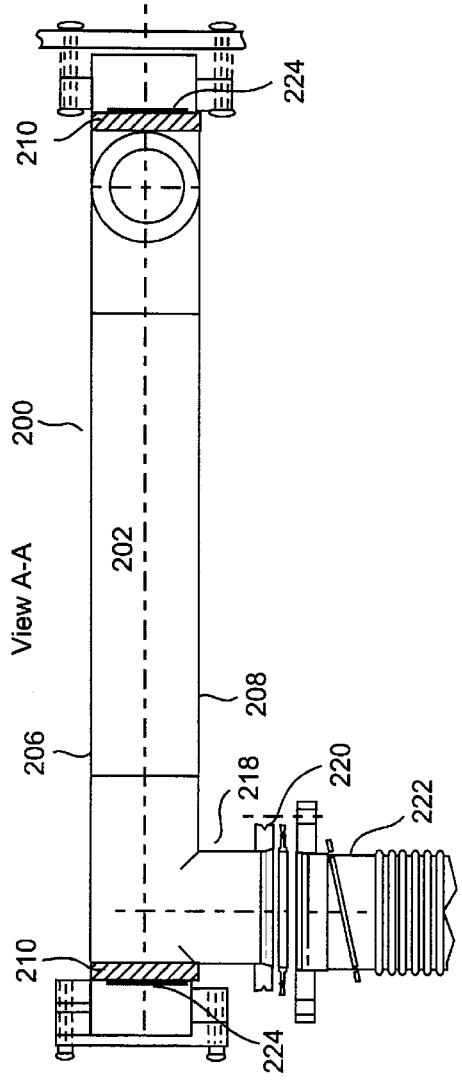

FIG. 2A illustrates a top sectional view of an exemplary in-line cell useful in absorption spectroscopy according to one aspect of the invention, and FIG. 2B shows a side-sectional view taken along line A—A of FIG. 2A. While the exemplary cell is of the Herriott type of multipass cell, it should be clear that the inventive concepts described hereinbelow are in no way limited thereto, and can readily be applied to other forms of cells.

The in-line cell 200 includes a sample region 202, which is bounded by sidewalls 204, top wall 206 and bottom wall 208. Mirrors 210 are disposed at opposite ends of the cell, and have light reflective surfaces facing the sample region. The light reflective surfaces are preferably a polished metal. As a high reflectivity of these surfaces is desirable, the surfaces can be coated with one or more layers of a reflective material such as gold, other metallic layers or a highly reflective dielectric coating, in order to enhance the reflectivity thereof.

The cell further includes a light entry and exit port 212 for allowing a light beam to pass into the cell and to pass out of the cell. While the exemplary embodiment shows a single port through which the light beam enters and exits the cell, a plural port structure is also envisioned. Thus, the light beam can enter and exit the cell through the same or different ports in the cell, and can enter and/or exit the cell through plural light entry or light exit ports. Further, the ports can be disposed on the same side or different sides of the cell.

The entry/exit port 212 contains a light transmissive window 214 which allows the light beam to pass into and out of the sample region. Suitable light transmissive materials for the window are known and include, for example, aluminum oxide, quartz and magnesium fluoride. The mirrors 210 and light transmissive window 214 seal the cell in a substantially airtight manner. This makes possible the measurement of gas samples at low pressures, i.e., at vacuum conditions, thereby allowing for in-situ measurements in vacuum processing tools such as used in the semiconductor manufacturing industry.

As shown in the exemplified cell, light entry and exit port 212 and light transmissive window 214 can be incorporated into the mirror. With such a structure, the size of the cell can be minimized. Of course, a window which is distinct from the entry and/or exit port can be provided.

Light transmissive window 214 can additionally be provided with a coating layer on a surface opposite the surface facing the sample region for reflecting a portion of the light beam. Subtracting the signal due to the reflected portion of the beam from that of the transmitted portion can result in more accurate absorption measurements than otherwise possible. Among the commercially available coating materials, metallic coatings are preferred.

As shown in the exemplified embodiment, light transmissive window 214 can be offset at an angle from perpendicular relative to the incoming light beam, with the Brewster angle being preferred. By offsetting the window in this manner, coherent interference caused by the reflected portion of the beam can be avoided. As a result, measurement of greater accuracy can be obtained.

Such an offset can further serve the same purpose as that served by the optional coating layer described above. That is, the reflected portion of the beam can be used to obtain a more accurate measurement by subtracting out the signal due to background noise.

The exemplified in-line cell further includes a sample inlet port 216 and flange 218 for connection to a source for the sample to be measured. Inlet port 216 can advantageously be connected to an exhaust line from a semiconductor processing tool in order to perform in-situ measurements, for example, to determine concentrations of molecular gas species in the tool exhaust.

The gas sample passes through the cell from inlet port 216 into sample region 202 and out of the cell through exhaust port 218. The exhaust port can be connected to a suitable vacuum pump. The connection with the pump can be made using flange 220 and flexible hose 222.

To minimize the adverse effects an absorption signal caused by deposits formed on the light reflective surfaces, one or more heaters 224 for heating the light reflective surfaces of the mirrors are provided. The heater should be capable of raising the mirror's light reflective surface to a temperature of from about 50 to 150° C., preferably from about 70 to 100° C., although optimal temperatures are process dependent.

Suitable heaters include, but are not limited to, resistance-type heaters, self-regulating-type heaters such as heat trace, heating lamps, inductive heaters and liquid or gaseous heating fluids which optionally can be circulated.

The cell is constructed in such a fashion that the mirrors can be maintained at a temperature higher than that of nearby surfaces in the cell which are exposed to the atmosphere to be analyzed. Since the deposits tend to form on lower temperature surfaces, deposits can be effectively prevented from forming on the heated mirror surface facing the sample region.

Heating of the mirrors as described above should be contrasted with the situation in which the entire cell is heated. In such a case, heat transfer from the body of the cell to the mirrors is not facilitated. Consequently, the mirrors would tend to be at a lower temperature than the walls of the cell, resulting in deposits being concentrated on the mirrors.

A particularly advantageous way to achieve the objectives of the invention is by the integration of the one or more mirrors into one or more walls of the cell, with the heater(s) being disposed outside of the cell. This allows heat to be directly applied to the back-surface of the mirror. In this manner, it is possible to attain the objective of maintaining the mirror surface at a higher temperature than other surfaces in the cell, while at the same time, isolating the heater from the aggressive environment in the sample region. This is especially desirable since placement of the heater directly in the sample region would result in corrosion or other damage to the heater.

In the exemplified cell, mirrors 210 are integrated into the end flanges of the cell. The mirrors can be fixed in place by known methods, such as welding, to ensure a substantially air-tight seal. Integration of the mirrors into the walls of the cell is not, however, limited to the exemplified method.

The mirror itself, or any mirror mount which provides sufficient heat conduction and makes good thermal contact with the mirror, can be brought into direct physical (and thermal) contact with a heating element or, as in the case with lamp-type heaters, into direct thermal contact with the heating element located outside the cell. Generally, as long as the thermal resistance of the path from the heater to the mirror surface is less than the thermal resistance from the heat path to other surfaces inside the sample cell (or any nearby region), then the desired results can be achieved.

In addition to the above-described mirror heaters, a purge gas flow can optionally be introduced into the cell to further prevent the accumulation of deposits on the light reflective surfaces. Suitable purge gases include an inert gas, such as nitrogen, argon or helium. If the purge gas is heated, it can serve the purpose of the mirror heater described above. Preferably, such heated gas is localized on the light reflective surface. Therefore, such a heated purge gas stream can be used by itself or together with other types of heaters such as described above, to effectively prevent deposits on the light reflector surfaces. For an unheated purge gas stream, it is preferable to localize the flow of the gas in the vicinity of the light reflective surface. By minimizing flow of the purge gas, the need for retrofitting vacuum systems with larger capacity pumps will be eliminated.

In addition to the heating of the mirrors, the light transmissive windows can optionally be heated. In the exemplified cell, light transmissive window 214 can be heated using the same heater or a heater independent of that used to heat the mirror. Furthermore, a purge gas stream as described above with reference to the light reflective surface, can also be applied to the light transmissive window. By use of such a structure, deposits can be further prevented from forming on the windows.

Although the exemplified in-line cell is of a Herriott design, the inventive concepts can readily be applied to other types of in-line cells. For example, the inventive concepts can be applied to polygonal multipass cells or to any form of cell which is amenable to the above conditions with respect to the mirror and heater structures.

The in-line cell should be constructed of materials which are compatible with the atmospheres being contained therein. Such materials are within the knowledge of persons skilled in the art. For example, various forms of stainless steel can be used for cell surfaces which contact the sample being measured.

Figure 1:
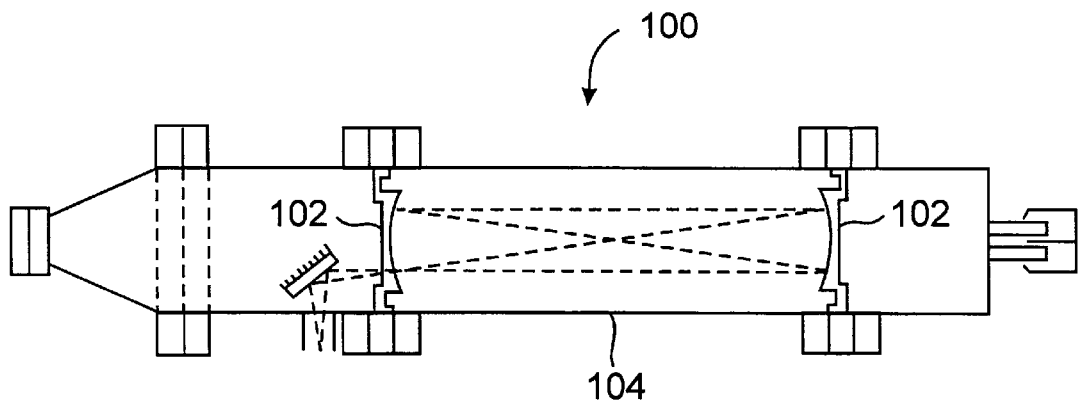
FIG. 1 is a conventional absorption spectroscopy cell according to the Herriott design.
Figure 3:
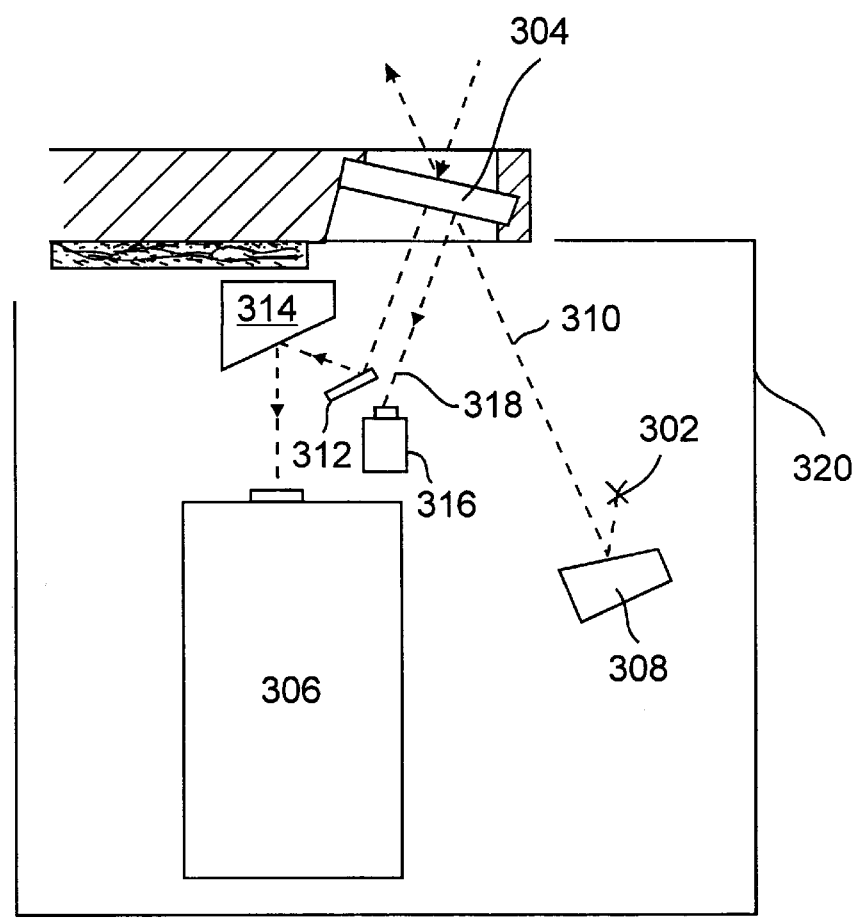
FIG. 3 is a top view of a light source/detector scheme in a system for performing an absorption spectroscopy measurement according to one aspect of the present invention.

While the inventive cell can be used for any absorption spectroscopy technique, it is preferably used in tunable diode laser absorption spectroscopy (TDLAS). With reference to FIG. 3, such a system includes, in addition to the in-line cell as described above with reference to FIGS. 2A and 2B, a light source 302, preferably a diode laser, for generating a light beam which is directed through the light transmissive window 304 into the sample region of the cell. To measure the light beam which exits the cell through the light transmissive window, the system further includes a main detector 306, which can be, for example, a photodiode.

Any molecular impurity of interest can be detected, subject only to the availability of a suitable light source. For example, water vapor, nitric oxide, carbon monoxide and methane or other hydrocarbons can be detected by measuring the attenuation of light from a diode laser source which emits light of a wavelength characteristic of the impurity.

Laser light sources which emit light in spectral regions where the molecules of interest absorb most strongly lead to improvements in measurement sensitivity. In particular, light sources which emit at wavelengths longer than about 2 $\mu$m are preferred, since many of the molecular impurities of interest have strong absorption bands in this region.

Any suitable wavelength-tunable light source can be used. Of the currently available light sources, diode laser light sources are preferred because of their narrow linewidth (less than about $10^{-3}$ cm$^{-1}$) and relatively high intensity (about 0.1 to several milliwatts) at the emission wavelength.

Examples of diode lasers include Pb-salt and GaAs-type diode lasers. The Pb-salt-type laser requires cryogenic temperatures for operation and emits infrared light (i.e., wavelength greater than 3 $\mu$m), while the GaAs-type diode laser can operate at close to room temperature and emits in the near infrared region (0.8–2 $\mu$m).

Recently, diode lasers which include Sb in addition to GaAs (or other pairs of III-V compounds such as AsP) have been described (see, "Mid-infrared wavelengths enhance trace gas sensing," R. Martinelli, Laser Focus World, March 1996, p. 77). These diodes emit light of a wavelength greater than 2 $\mu$m while operating at $-87.8°$ C. While such a low temperature is not convenient, it compares favorably with the cryogenic temperatures (less than $-170°$ C.) required by Pb-salt lasers.

Operation of similar lasers at 4 $\mu$m and 12° C. has also been reported (see, Lasers and Optronics, March 1996). Diode lasers of the above described type will most preferably operate at temperatures of at least $-40°$ C. Use of a thermoelectric cooler for temperature control at such temperatures makes these light sources less complicated than the lower temperature diode systems.

To make use of these lasers more desirable, improvement in the optical properties over current levels is important. For example, single mode diodes (i.e., diodes whose emission at fixed temperature and drive current is at a single wavelength with emission at other wavelengths at least 40 dB less intense) should be available.

Suitable light sources for use in the invention are not limited to the above described diode lasers. For example, other types of lasers which are similarly sized and tunable by simple electrical means, such as fiber lasers and quantum cascade lasers, are envisioned. The use of such lasers as they become commercially available is envisioned.

The system can further include at least one mirror 308 for reflecting the light beam 310 from the light source 302 through the light transmissive window into the cell, and at least one additional mirror 312, 314 for reflecting the light beam exiting the cell to the main detector.

The mirror 308 is preferably curved in order to collimate the light beam as the light from the diode laser source is divergent. Likewise, mirror 314 is preferably curved in order to focus the parallel light beam on the main detector.

A second detector 316, which can also be a photodiode, for measuring a portion of the light beam 318 which is reflected from the light transmissive window 304 as well as means for subtracting this reference signal from a measurement obtained by the main detector can optionally be provided in the system. An operational amplifier in a configuration such as described in the literature (See, e.g., Moore, J. H. et al "Building Scientific Apparatus", Addison Wesley, London, 1983) can act as the means for subtracting the reference signal.

The reflected light does not show any absorption by the molecules of interest in the sample region, and therefore provides a reference signal. By subtracting the reference signal from that of the light which passes through the cell (which is measured by the main detector), variations in the light source can be compensated for. This also allows for enhanced sensitivity to signal changes due to molecules in the system chamber 320.

While "dual beam" techniques using subtraction of a reference beam are well-known they usually require a dedicated beam-splitter, i.e., an optical element whose only function is to divide the light beam. According to the present invention, the entrance window to the chamber can provide this function without the need for any additional components. The ratio of transmitted to reflected light at this window can be controlled by use of an appropriate coating for the window.

The inventive system has particular applicability in detecting a molecular species in a gas exhausted from a vacuum chamber. In such a case, the cell can be disposed in a vacuum exhaust line between a vacuum chamber and a vacuum pump system.

The system is compatible with a wide range of materials. For example, the vacuum chamber can contain certain reactive or nonreactive (inert) gas species which can be in a plasma- or non-plasma state. Examples of reactive gases which are compatible with the inventive system include $SiH_4$, HCl and $Cl_2$ provided the moisture level is less than 1000 ppm. Any inert gas such as, e.g., $O_2$, $N_2$, Ar and $H_2$ can be used in the inventive system. In the case of the inventive system's use in a plasma environment, the system is preferably mounted about 6 inches or more away from the plasma zone in order to minimize the formation of deposits on the windows and other cell surfaces.

Because the detection system described above can be used in plasma or non-plasma atmospheres as well as with inert or reactive gases, the system is particularly well suited for use in monitoring gas phase molecular species, such as water vapor, in a semiconductor processing apparatus. Use of the detection system in conjunction with a semiconductor processing apparatus allows for real time in-situ monitoring of gas phase molecular impurities.

The system can be readily adapted to virtually any semiconductor processing apparatus which employs a vacuum system. Examples of such apparatuses include etching, diffusion, chemical vapor deposition (CVD), ion implantation, sputtering and rapid thermal processing apparatuses.

Figure 4:
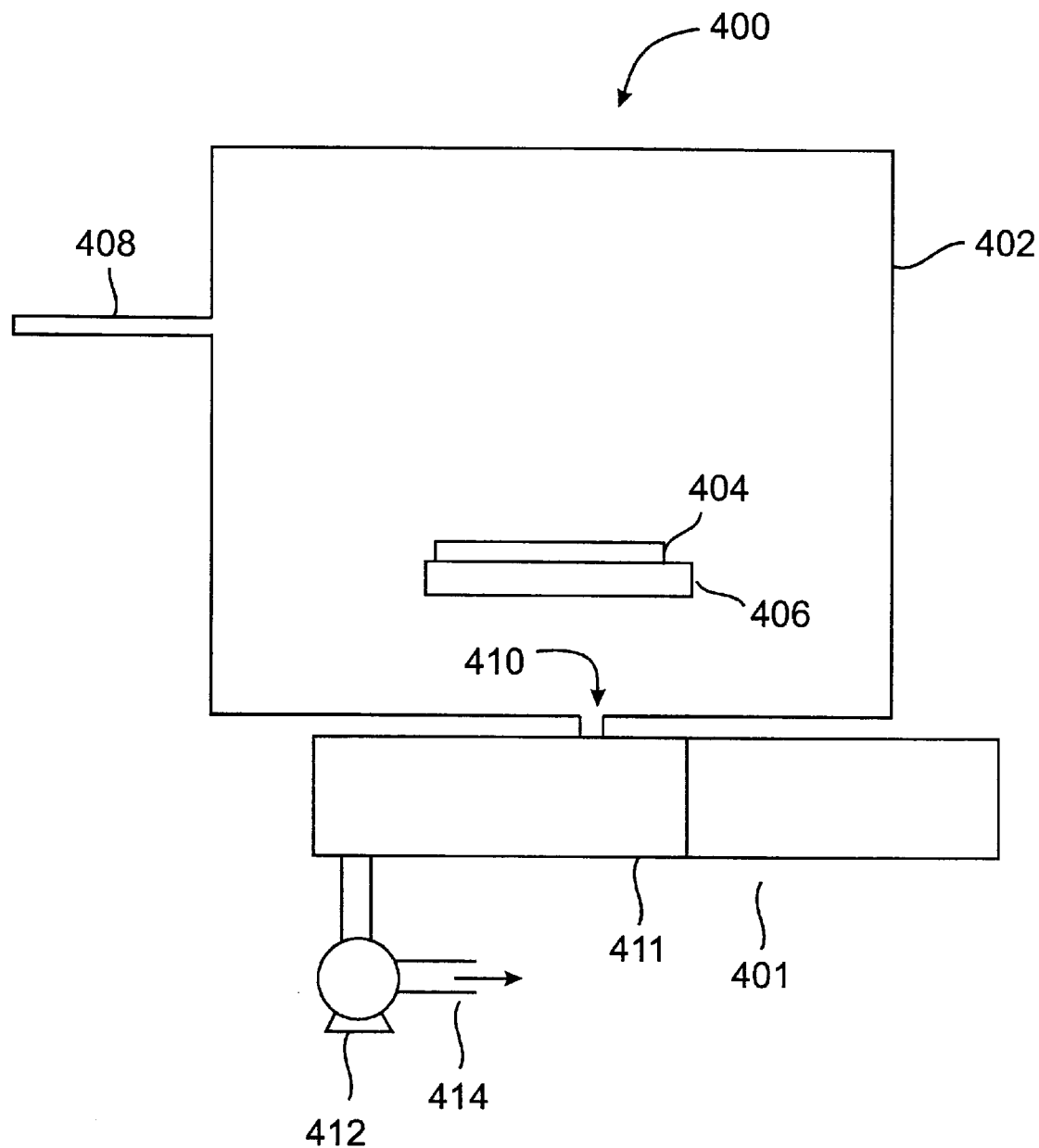
FIG. 4 is a side sectional view of a semiconductor processing apparatus which includes a system for performing an absorption spectroscopy measurement in accordance with the invention.

FIG. 4 illustrates a semiconductor processing system 400 which comprises an in-line cell and system 401 for performing absorption spectroscopy measurements as described in detail above. The system further includes a vacuum chamber 402 inside which a semiconductor substrate 404 is disposed on a substrate holder 406. One or more gas inlets 408 are provided for delivering a gas or plural gases to the vacuum chamber.

The vacuum chamber is evacuated through an exhaust opening 410 in the vacuum chamber. A portion of the total exhaust from the processing tool or the entire exhaust volume can be introduced into cell 411. A vacuum pump 412 for evacuating the vacuum chamber is connected thereto, either directly or through a vacuum line. A pump exhaust line 414 can be connected to the pump 412, which can be connected to another pump or to a gas scrubber (not shown). Examples of vacuum pumps which may be employed are mechanical rotary and booster pumps, diffusion pumps, cryogenic pumps, sorption pumps and turbomolecular pumps.

Furthermore, while the vacuum pump and measurement system have been illustrated as being disposed below the vacuum chamber, those skilled in the art readily understand that other orientations are also possible.

While the invention has been described in detail with reference to specific embodiments thereof, it will be apparent to one skilled in the art that various changes and modifications can be made, and equivalents employed, without departing from the scope of the appended claims.

What is claimed is:

1. An in-line cell useful in absorption spectroscopy, comprising a sample region, a light entry port in communication with the sample region to allow a light beam to enter the cell and pass through the sample region, a light exit port in communication with the sample region to allow a light beam after passing through the sample region to exit the cell, the light entry port and light exit port being the same or separate ports, each said port containing a light transmissive window, a mirror having a light reflective surface facing the sample region for reflecting a light beam within the cell, and a heater effective to heat the light reflective surface of the mirror.

2. The in-line cell according to claim 1, wherein the heater is disposed outside of the cell.

3. The in-line cell according to claim 1, wherein the heater is in direct contact with a back surface of the mirror.

4. The in-line cell according to claim 1, wherein the thermal resistance of a path from the heater to the mirror is less than the thermal resistance of a path from the heater to other surfaces of the sample cell.

5. The in-line cell according to claim 1, wherein the heater is a resistance-type heater.

6. The in-line cell according to claim 1, wherein the cell is a multipass cell.

7. The in-line cell according to claim 1, further comprising a purge gas inlet effective to introduce a purge gas stream which contacts the mirror.

8. The in-line cell according to claim 1, further comprising a heater for heating each light transmissive window.

9. The in-line cell according to claim 1, wherein the light transmissive window in the light entry port is offset from perpendicular with respect to an incoming light beam.

10. The in-line cell according to claim 1, wherein the light reflective surface is integrated into a wall of the cell.

11. A system for performing an absorption spectroscopy measurement, comprising:

a sample region, a light entry port in communication with the sample region to allow a light beam to enter the cell and pass through the sample region, a light exit port in communication with the sample region to allow a light beam after passing through the sample region to exit the cell, the light entry port and light exit port being the same or separate ports, each said port containing a light transmissive window, a mirror having a light reflective surface facing the sample region for reflecting a light beam within the cell, and a heater effective to heat the light reflective surface of the mirror, and a light source for generating a light beam which passes through the light entry port into the cell, and a main detector for measuring the light beam exiting the cell through the light exit port.

12. The system according to claim 11, wherein the heater is disposed outside of the cell.

13. The system according to claim 11, wherein the heater is in direct contact with a back surface of the mirror.

14. The system according to claim 11, wherein the thermal resistance of a path from the heater to the mirror is less than the thermal resistance of a path from the heater to other surfaces of the sample cell.

15. The system according to claim 11, wherein the heater is selected from the group consisting of resistance-type heaters, self-regulating-type heaters, heating lamps, inductive heaters and a heating fluid.

16. The system according to claim 11, further comprising a purge gas inlet effective to introduce a purge gas stream which contacts the mirror.

17. The system according to claim 11, further comprising a heater for heating each light transmissive window.

18. The in-line cell according to claim 11, wherein the light transmissive window in the light entry port is offset with respect to an incoming light beam from perpendicular.

19. The system according to claim 11, wherein the cell is disposed between and in communication with a vacuum chamber and a vacuum pump.

20. A semiconductor processing apparatus, comprising:

a vacuum chamber in communication with a vacuum pump for evacuating the vacuum chamber, an in-line cell disposed between and in communication with the vacuum chamber and the vacuum pump, the cell comprising a sample region, a light entry port and a light exit port being the same or separate ports, each said port being in communication with the sample region and containing a light transmissive window, a mirror having a light reflective surface facing the sample region, and a heater effective to heat the light reflective surface of the mirror a light source for directing a light beam through the light entry port into the cell, and a main detector for measuring the light beam exiting the cell through the light exit port.

* * * * *